ELECTRONIC DEMAND HEART PACEMAKER WITH DIFFERENT PACING AND STANDBY RATES

Original Filed Jan. 7, 1970 2 Sheets-Sheet 1

INVENTOR.
DAVID H. GOBELI
BY
Lew Schwartz
ATTORNEY

INVENTOR.
DAVID H. GOBELI
BY
Lew Schwartz
ATTORNEY

United States Patent Office

Re. 28,003
Reissued May 7, 1974

28,003

ELECTRONIC DEMAND HEART PACEMAKER WITH DIFFERENT PACING AND STANDBY RATES

David H. Gobeli, Minneapolis, Minn., assignor to Medronic, Inc., Minneapolis, Minn.

Original No. 3,656,487, dated Apr. 18, 1972, Ser. No. 1,178, Jan. 7, 1970, which is a continuation-in-part of abandoned application Ser. No. 832,706, June 12, 1969. Application for reissue June 30, 1972, Ser. No. 267,961
Int. Cl. A61n *1/36*
U.S. Cl. 128—419 P 20 Claims

Matter enclosed in heavy brackets [ ] appears in the original patent but forms no part of this reissue specification; matter printed in italics indicates the additions made by reissue.

ABSTRACT OF THE DISCLOSURE

A demand type heart pacer which provides electronically generated stimulating pulses to the heart at a first frequency in the continued absence of natural heartbeats, but which inhibits output pulses once the natural heart rate exceeds the first frequency, and allows the heart to beat naturally at any rate above a second, lower frequency before again providing stimulating pulses, thereby creating a different standby frequency. The pacer also reverts to a third frequency in a non-demand type operation in the presence of an interfering electrical noise pattern.

BACKGROUND OF THE INVENTION

This invention is concerned with electronic heart pacing apparatus, and in particular a demand type heart pacer. Demand pacers are known in the art to be the type of pacer which provides electrical pulses to stimulate the heart only in the absence of normal heartbeats. An *example of a prior art demand pacer is found in United Kingdom Pat. No. 826,766 issued to National Research Development Corporation on an invention of John Geoffrey Davies for Device for Stimulating Periodic Functions of the Body.* Prior art demand pacers typically generate pulses at a fixed frequency, the generated pulses being prevented if a natural heartbeat appeared during the period between generated pulses. As possible complications can occur if external electrical pulses are provided to a heart which is beating naturally, it would obviously be advantageous for the heart monitoring pacer to be able to wait a longer period of time than that provided by its normal pulse generation frequency, once a natural heartbeat has occurred, to be certain that it does not provide an unnecessary external pulse. Yet, the heart monitoring pacer must be certain not to allow the heatrbeat rate to fall below a minimum frequency. The apparatus of this invention provides, with novel circuitry, the advantages described above, and in addition provides circuitry for eliminating dangers due to continuous external noise electrical signals which may enter the electrical system of the demand pacer.

SUMMARY OF THE INVENTION

Briefly described, the apparatus of this invention comprises a demand pacer having a pulse generator and an amplifier connected to the heart through a pair of electrodes. The pulse generator provides controlled pulses to the heart through the electrodes, while the amplifier senses signals from the heart through the electrodes, for controlling the pulse generator. The normal frequency of the pulse generator is controlled by apparatus including the charging time of a capacitor. In a first embodiment of this invention further apparatus including another capacitor is connected between the pulse generator and the sensing amplifier. This second capacitor is selectively connected in parallel with the pulse generator frequency determining capacitor on occurrence of a natural heartbeat, and thus increases the charging time of the capacitance for the pulse generator frequency determining apparatus, to thus lower the frequency of pulses generated. When no natural heartbeat occurs, the second capacitor is not connected to the pulse frequency determining capacitor, and the pulse generator runs at its fixed higher frequency. In a second embodiment of this invention the further apparatus is connected to the output of the pulse generator such that the second capacitor is selectively charged during each stimulating pulse to the heart. The second capacitor is connected to the pulse generator frequency determining capacitor so as to add its charge to that of the power supply and thus decrease the charging time, to increase the frequency of the pulse generator in the absence of a natural heartbeat.

Therefore, the demand pacer apparatus of this invention will proceed to supply pulses to the heart at a normal pacing rate of a first frequency until it senses an ectopic beat, after which it will wait a longer period than the normal pacing frequency period before it pulses again. If no further ectopic beats are sensed it will return to the normal pacing rate after the next generated pulse. It is important to note that with an irregular heart rate causing many ectopic beats, the apparatus of this invention will be alternately inhibited and then pacing. However, the minimum average pacing rate must be the standby pacing rate. Further, any sinus rhythm above the standby rate completely inhibits the unit. Therefore, the apparatus of this invention will allow normal sinus rhythm to control at a rate below or above its own normal pacing frequency, yet provides a minimum rate determined by the standby frequency unless repetitive interference is present. When such interference occurs, the pacer circuitry causes the device to revert to asynchronous operation at a rate somewhat lower than the standby rate.

DESCRIPTION OF THE PREFERRED EMBODIMENTS

Figure 1:
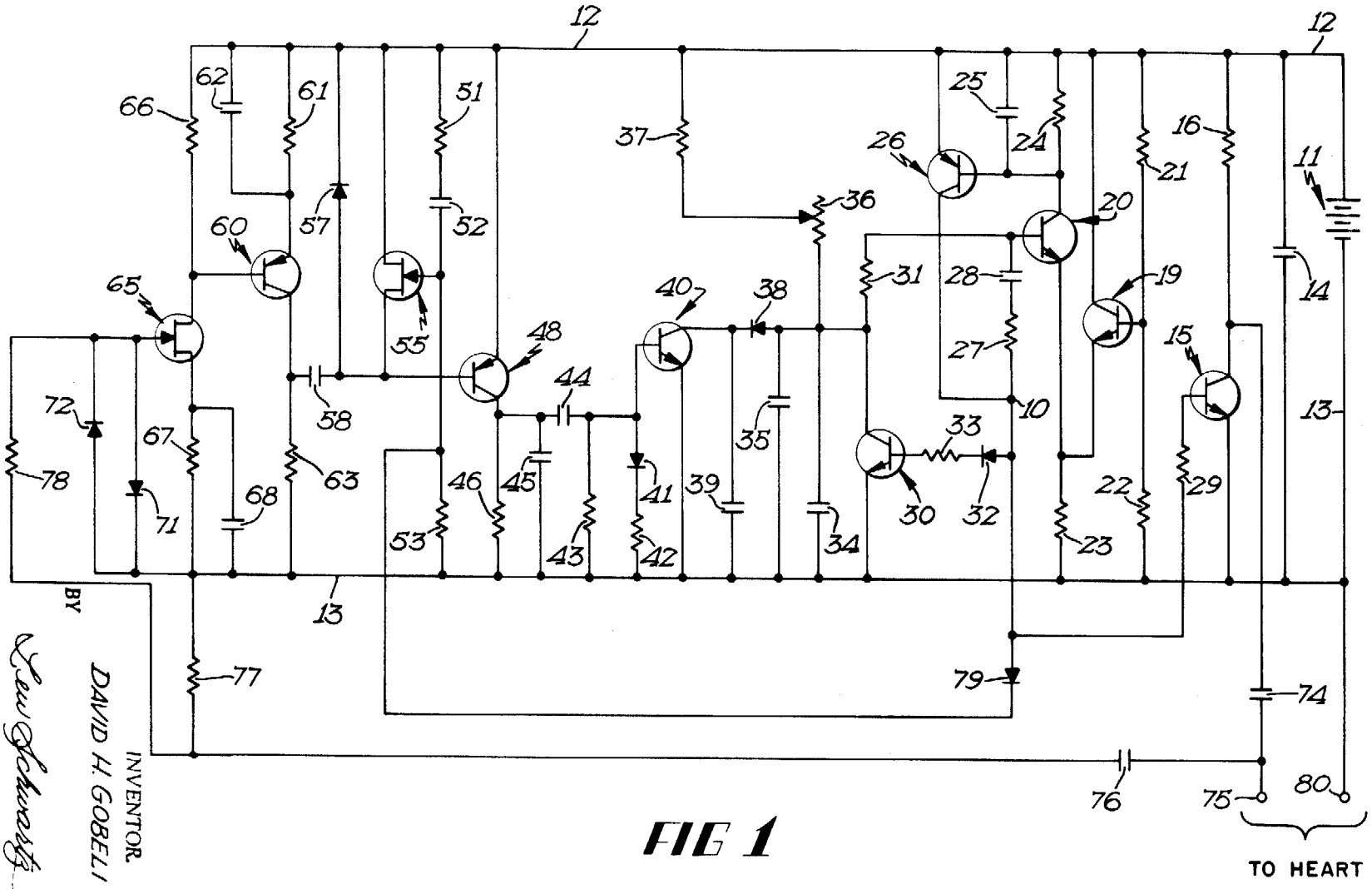
FIG. 1 is a schematic diagram showing the electronic circuitry of a first embodiment of the apparatus of this invention.

In FIG. 1 there is shown a source of energy here shown as a power supply comprising batteries 11. The positive terminal of supply 11 is connected to a positive bus 12, while the negative terminal of supply 11 is connected to a negative bus 13. A capacitor 14 is connected between busses 12 and 13 for supply regulation purposes, in a manner well known to those skilled in the art. A transistor 15 has an emitter connected to negative bus 13, and a collector connected through a resistor 16 to positive bus 12.

There are also shown a pair of transistors 19 and 20, each having an emitter connected through a resistor 23 to negative bus 13. The collector of transistor 19 is connected to positive bus 12, while the base of transistor 19 is connected through a resistor 21 to bus 12 and through a resistor 22 to bus 13. The collector of transistor 20 is connected through a resistor 24 to bus 12, and through a capacitor 25 to bus 12.

A transistor 26 has an emitter connected directly to bus 12, a base connected to the collector of transistor 20, and a collector connected to a junction 10. Junction 10 is connected through a serial combination of a resistor 27 and a capacitor 28 to the base of transistor 20.

A transistor 30 has an emitter connected to negative bus 13, a collector connected through a resistor 31 to the base of transistor 20, and a base connected through a serial combination of a resistor 33 and a diode 32 to junction 10. Junction 10 is also connected through a resistor 29 to the base of transistor 15.

The collector of transistor 30 is also connected to a variable resistor 36. The wiper arm of resistor 36 is connected through a resistor 37 to positive bus 12. The collector of transistor 30 is connected to negative bus 13 through each of a pair of capacitors 34 and 35.

A transistor 40 has an emitter connected to negative bus 13, a collector connected through a diode 38 to the collector of transistor 30, and a base connected through the serial combination of a diode 41 and a resistor 42 to negative bus 13. The collector of transistor 40 is also connected through a capacitor 39 to bus 13, while the base of transistor 40 is also connected to bus 13 through a resistor 43.

A transistor 48 has an emitter connected to positive bus 12, and a collector connected through a resistor 46 to negative bus 13. The collector of transistor 48 is also connected to negative bus 13 through a capacitor 45, and is connected to the base of transistor 40 through a capacitor 44. A resistor 51, a capacitor 52 and a resistor 53 are serially connected between positive bus 12 and negative bus 13. A field effect transistor 55 has a gate connected to a junction between capacitor 52 and resistor 53, a source connected to positive bus 12, and a drain connected to the base of transistor 48. A diode 57 is connected between the source and drain of field effect transistor 55.

A transistor 60 has an emitter connected to positive bus 12 through each of a resistor 61 and a capacitor 62. The collector of transistor 60 is connected through a resistor 63 to negative bus 13, and through a capacitor 58 to the base of transistor 48. The base of transistor 60 is connected through a resistor 66 to positive bus 12.

A field effect transistor 65 has a drain connected to the base of transistor 60, and a source connected to negative bus 13 through each of a resistor 67 and a capacitor 68. The gate of field effect transistor 65 is connected to negative bus 13 through each of a pair of oppositely poled diodes 71 and 72.

The collector of transistor 15 is connected through a capacitor 74 to an electrode 75. Electrode 75 is connected through the serial combination of a capacitor 76 and a resistor 78 to the gate of field effect transistor 65. A resistor 77 is connected from a point intermediate capacitor 76 and resistor 78 to negative bus 13. Another electrode 80 is connected to negative bus 13. Finally, junction 10 is connected through a diode 79 to the junction between capacitor 52 and resistor 53.

To best understand the operation of the apparatus shown in FIG. 1, assume that no natural heartbeats have been present and that the pulse generator of the pacer has been running at its normal repetition rate. Assume also that an output pulse has just been completed.

The pulse generator can be generally described as including transistors 19, 20, 26 and 30, along with their associated components including in particular capacitors 28 and 35. Transistor 15 comprises the output transistor.

During the last output pulse, capacitor 74 will have discharged for a period of time determined by the pulse generator. With the pulse generator off during the period between pulses, transistor 15 will be off, and capacitor 74 will recharge through the path comprising battery 11, bus line 12, resistor 16, capacitor 74 itself, the heart through electrodes 75 and 80, and through bus line 13 to battery 11. This will cause the plate of capacitor 74 connected to the collector of transistor 15 to be positive with respect to its opposite plate.

As capacitor 74 is charging, so will be capacitor 35. Capacitor 35 is charged through variable resistor 36 and resistor 37. As capacitor 39 will have charged at some previous time, and will not have discharged during the last pulse in the absence of a natural heartbeat, for reasons more fully described below, capacitor 39 will have no significant affect on the time for the charge of capacitor 35. Capacitor 34 is selected to be an RF bypass capacitor to prevent turn-on of the pulse generator from stray pick-up, and will, therefore, be sufficiently smaller than capacitor 35 so as to be essentially ignored in considering the timing of the pulse generator.

Transistors 19 and 20 are connected in a well known differential amplifier manner to provide temperature compensation for the turn-on point of transistor 20, to maintain substantially constant timing for the pulse generator. Resistors 21, 22, 23 and 24 act as bias resistors for transistors 19 and 20. Capacitor 25 is a bypass capacitor connected across resistor 24.

When capacitor 35 becomes sufficiently charged, the positive potential felt across it will be felt at the base of transistor 20 to turn it on. The turn-on of transistor 20 will cause a drop in its collector voltage which will be felt at the base of transistor 26 to turn it on. The turn-on of transistor 26 will cause a positive potential from bus line 12 to be felt at junction 10. This positive potential at junction 10 will cause several actions.

First, the positive potential at junction 10 will be felt through capacitor 28 to provide positive feedback to the base of transistor 20 to turn it on strong and keep in on. Second, the positive potential at junction 10 will be felt through diode 32 and resistor 33 on the base of transistor 30 to turn it on, causing the discharge of capacitor 35. Thirdly, the positive potential at junction 10 will be felt through resistor 29 on the base of output transistor 15 to turn it on, causing capacitor 74 to discharge through the collector-emitter path of transistor 15, and through electrode 80 to the heart and back through electrode 75 to capacitor 74. Finally, the positive potential at junction 10 will be felt through diode 79 to cause an inhibit signal to prevent the preamplifier from sensing the pacemaker pulse as though it were a natural heartbeat, or R wave, in a manner to be more fully described below.

The turn-on of transistor 30 will quickly discharge capacitor 35, and transistor 30 will stay on until the positive potential disappears at junction 10. The positive potential to junction 10 will remain as long as transistor 26 is on, which is determined by the one time of transistor 20. Transistor 20 will remain on for a period of time determined by the charge time of capacitor 28, through which the positive potential at junction 10 is felt. Therefore, the charge time of capacitor 28 determines the on time of the pulse generator, thus determining the on time of output transistor 15 and the output pulse width.

When capacitor 28 has charged sufficiently so that the potential on the base of transistor 20 is no longer sufficient to keep it on, transistor 20 will turn off to turn off transistor 26 and remove the positive potential from junction 10, thus causing the turnoff of transistor 30 and output transistor 15. Capacitors 74 and 35 will then again begin to charge in the manner described above, and the pulse generator cycle will be repeated, provided no natural heartbeat occurs, as described below.

The implifier of the pacer of FIG. 1 comprises field effect transistor 65, transistor 60 and 48, and their associated circuit components. Resistors 46, 61, 63, 66 and 67 are bias resistors for their respective transistors. Capacitors 62 and 68 are bypass capacitors. Field effect transistor 65, and transistor 60, are so biased as to be class A amplifiers and to amplify input signals of either polarity. Resistor 77 is a DC bias reference for the gate of field effect transistor 65. Resistor 78 is a limiting resistor and works with diodes 71 and 72 to limit the input voltage to the gate of field effect transistor 65.

When a pulse of either polarity appears at electrode 75, it will be felt through capacitor 76 and resistor 78 across the parallel combination diodes 71 and 72. As field effect transistor 65 is class A biased, a pulse of either polarity, limited by diodes 71 and 72 along with resistor 78, will be amplified by it. This will cause a change of potential on the drain electrode of field effect transistor 65, which will in turn be felt on the base of class A amplifier connected transistor 60 and further amplified by it. Transistor 60 will then have a change of potential at its collector, which will be differentiated and passed through capacitor 58 to the base of transistor 48. In the embodiment shown in FIG. 1, transistor 48 is class C connected, and will turn on when the negative portion of the differentiated signal through capacitor 58 reaches the base of transistor 48. Diode 57 will prevent capacitor 58 from eventually charging due to a series of negative going potential changes at the collector of transistor 60.

The turn-on of transistor 48 causes its collector to go positive. This positive signal passes through a reversion to fixed rate circuit which will be more fully described below. For the present, it is sufficient to recognize that the positive signal will pass through capacitor 44 to the base of transistor 40 to turn it on. The turn-on of transistor 40 causes an interruption of the normal charge cycle of capacitor 35 and changes the pacer to its standby or sentinel frequency which is lower than that of the normal frequency of the pulse generator. This circuitry will also be more fully described below.

The above-described amplifier has a refractory period primarily caused by bypass capacitors 62 and 68. These capacitors are chosen to be of a value so that they will charge during the presence of an input signal passing through the amplifier, and the discharge time of capacitors 62 and 68 will constitute a refractory period for the amplifier. The capacitors must be chosen with care as they will also affect the gain of the amplifier.

As has been described above, a pulse of either polarity appearing at electrode 75 will be felt through the amplifier to affect the frequency of the pulse generator. To prevent this from occurring when the pulse at electrode 75 is the pacemaker generated pulse rather than a natural heartbeat or R wave, an inhibit circuit is provided which comprises field effect transistor 55 and its associated components resistor 51, capacitor 52 and resistor 53. As has been described above, the positive potential at junction 10 which turns on output transistor 15 will also be felt through diode 79 to the inhibit circuit. This positive potential will be felt on the gate of field effect transistor 55 to raise the gate potential to substantially that of the source potential of field effect transistor 55, thus removing the reverse bias and turning on field effect transistor 55. This will cause a positive potential to be felt on the base of transistor 48 thus holding it off and inhibiting any pulse from the amplifier from passing through to the pulse generator. The amplifier will have a small recovery pulse appearing at the base of transistor 48 following its refractory period, due to the charge and discharge of capacitors 62 and 68, but this recovery pulse is not of sufficient magnitude to turn on transistors 48 and 40 unless repetitive interference is present as will be more fully described below. Capacitor 52 is provided to hold on field effect transistor 55 for a period of time sufficient to prevent the [pacemaker] *pacer* pulse from turning on transistor 48 but to allow the recovery pulse to be transmitted to the base of transistor 48. Capacitor 52 will be discharged by the pulse appearing from junction 10 through diode 79, and in recharging will keep a positive potential on the gate of field effect transistor 55 to keep it on for a period of time determined by the resistance present in the charging path of capacitor 52. Thus, the pacer of FIG. 1 will prevent its normal pulse generator output frequency from being affected by sensing of its own output pulse.

There has been described above the operation of the apparatus by which the pulse generator of FIG. 1 provides heart stimulating pulses at a fixed frequency, and how the sensing portion of the apparatus is inhibited from interrupting the operation of the pulse generator at the fixed frequency when the generated pulses themselves are sensed. However, as has been stated above, it is the purpose of the apparatus of this invention, once a natural heartbeat or R wave has been sensed, to lower the pulse generator frequency, that is, increase the cycle period between pulses, to give the heart an opportunity to beat naturally without stimulus pulses from the pacer, even though the heart rate should be lower than that of the normal pulse generator frequency. Also, the standby or lower frequency used when a heartbeat is detected becomes substantially the lowest frequency at which the heart will be allowed to beat in the absence of repetitive noise signals. That is, the standby frequency normally sets a lower limit of heartbeat rate, though the pacer as a whole will allow the heart to beat naturally between that lower standby rate and the higher normal pulse generator frequency rate.

For purposes of example, assume the normal pulse generator frequency to be such as to provide pulses for an equivalent heart rate of 72 b.p.m. If the apparatus of FIG. 1 is pacing, as in complete heart block, and the heart produces an ectopic beat after a previous pacer[pacemaker] pulse and the refractory period of the amplifier, but before the next pacer [pacemaker] pulse, the pulse generator will be reset. The pacer [pacemaker] will then pulse again at a time after the ectopic beat determined by the standby rate. If the heart continues natural beating at a rate greater than the standby rate, the pulse generator of the pacer [pacemaker] will be prevented from providing further pulses. However, if after the ectopic beat no other beat occurs within the standby rate period, for example 1,000 ms for a standby rate of 60 b.p.m. the pacer [pacemaker] will again provide a pulse at the end of this period. Then, if no further natural heartbeats are sensed, the unit will pulse again at the normal pulse generator frequency of 72 b.p.m., until another natural heartbeat is sensed. Thus, the apparatus of this invention, after sensing a natural heartbeat, waits for a period of time longer than the normal pacing frequency before it provides another heart stimulating pulse. If no more natural heartbeats are sensed, the pacer returns immediately, and during the next period of time between pulses, to the normal pacing rate.

The operation of the apparatus of FIG. 1 to achieve the standby rate will now be explained. Assume that a natural heartbeat of R wave appears at electrode 75. In the manner described above, this pulse will be felt through capacitor 76 and resistor 78 to pass through the amplifier of the apparatus of this invention. If this natural heartbeat of R wave appears at electrode 75 at a time when a generated pulse is not present and when the refractory period of the amplifier is completed, transistor 48 will be turned on, to turn on transistor 40 in the manner described above. When transistor 40 turns on, it provides a discharge path for capacitor 39. Note that in normal operation of the pulse generator, capacitor 39 will have charged through resistors 36 and 37 and diode 38. However, when transistor 30 is turned on to discharge capacitor 35, diode 38 will prevent the discharge of capacitor 39. Thus in normal operation only capacitor 35 has a substantial effect on the timing for the pulse generator. However, when transistor 40 is turned on to discharge capacitor 39, capacitor 35 will also discharge through diode 38 and transistor 40 and the pulse generator timing cycle will be completely reset. Further, current flowing through resistors 36 and 37 will now be divided between capacitors 35 and 39 until such time as diode 38 becomes reverse biased by the charge on capacitor 39. As the capacitance is increased by the addition of capacitor 39, and as the amount of current available through resistors 36 and 37 remains essentially the same, it will obviously take longer for capacitor 35 to charge to the potential where it will turn on transistor 20 of the pulse generator as described above. Therefore, it is apparent that each time a pulse passes through the amplifier to turn on transistor 40, the entire pulse generator cycle will be reset, and the next timing cycle will be at the standby rate which is a longer period than that of the normal pulse generator frequency. If another natural heartbeat appears during the standby period, the pulse generator will again be reset and prevented from providing a stimulating pulse, and the standby rate will again commence. Thus, as long as a natural heartbeat has appeared during the standby period, no stimulating pulse will be provided from the pacer, and following each natural heartbeat the pacer pulse generator will operate at the standby frequency. If a standby frequency period is completed without the appearance of a natural heartbeat, the pacer will provide a stimulating pulse and immediately return to the normal pacing frequency, provided no further natural heartbeats appear.

The apparatus of this invention also includes circuitry for automatically reverting to asynchronous operation at a third frequency of the pulse generator different from either the first or second frequencies when it is subjected to interference from electrical signals of a repetitive nature. To activate the reversion circuitry, such repetitive noise signals must have a repetition rate in excess of a designed minimum rate greater than the upper limit of normal heartbeat rates. In FIG. 1, this circuitry comprises diode 41, resistor 42 and resistor 43 as combined with coupling capacitor 44. The refractory period of the amplifier contributes to determination of the pulse generator frequency in the presence of such interference.

Assume, for example, that the apparatus of FIG. 1 is exposed to external electrical noise of a periodic nature, such as a sine wave, and that the sine wave enters the amplifier after its refractory period and so is felt at the collector of transistor 48. If such were the case and no noise protective circuitry were present, then the sine wave would be felt across coupling capacitor 44 and would turn on transistor 40 to continuously reset the pulse generator, which, of course, is not desirable. To prevent this continuous resetting of the pulse generator and consequent continuous inhibition of the pacer regardless of heart activity due to external noise, diode 41 serves to let the positive portion of the sine wave pass through resistor 42 to ground. The negative portion of this sine wave will see resistor 43, which is chosen to be of substantially larger resistance than resistor 42. Therefore, if a series of sine wave passes through capacitor 44, then capacitor 44 will sine wave and thereafter prevent the turn-on of transistor 48 being positive and the other plate negative. This positive charge facing the source of the sine waves will eventually block out further positive portions of the sine wave and thereafter prevent the turnon of transistor 40. However, if the time between positive pulses is great enough, such as in the range of normal heartbeat frequencies or during the refractory period of the amplifier, capacitor 44 will have sufficient time to discharge through resistor 43, to avoid blocking the next incident pulse and subsequent normally spaced heartbeat pulses.

It is thus apparent that whenever a source of noise, such as 60 cycle AC, is picked up by the apparatus of this invention, the pulse generator of this invention is immediately reset to the standby period and begins charging to fire as soon as capacitor 44 is substantially fully charged. When a pulse is fired by the pulse generator it is sensed by the amplifier but blocked by the inhibit circuit. Sensing of the pacemaker pulse makes the amplifier block other signals for its refractory period, during which capacitors 35 and 39 begin charging at the standby rate and capacitor 44 discharges. At the end of the refractory period, if repetitive interference is still present, it is superimposed on the recovery pulse of the amplifier and causes portions of the pulse to have a magnitude sufficient to rapidly and repetitively turn on transistors 48 and 40 until capacitor 44 becomes fully charged. Each turn-on of transistors 48 and 40 resets the pulse generator to its standby period again, but since capacitor 44 charges quickly and blocks subsequent interference pulses, the timing cycle begins again almost immediately. Consequently, the resetting action in the presence of repetive noise (once on output pulse generation and possibly several times in rapid succession on termination of the refractory period) has been simply called "double reset."

The pulse firing and double reset repeat so long as interference is present. Thus, in the presence of repetitive interference or noise, the pacer runs at a rate slower than either the normal rate or the standby rate and is not synchronized with natural heartbeats. The pacer pulse repetition period in the presence of repetitive noise signals is approximately the sum of the standby period and the amplifier refractory period. For example, if the standby period is 1,000 ms and the refractory period is 150 ms, the pacer period in the presence of repetitive interference is about 1,150 ms or a rate of about 52 bpm. This slowdown of the pacer accompanying its reversion to a synchronous operation in the presence of repetitive noise signals is very useful in testing the functioning of the unit after implantation. It can also be seen that the slowdown accompanying a reversion to a synchronous operation can be achieved in a demand pacer without the standby rate feature in a similar manner by double reset of the simpler timing circuit used in such devices.

Figure 2:
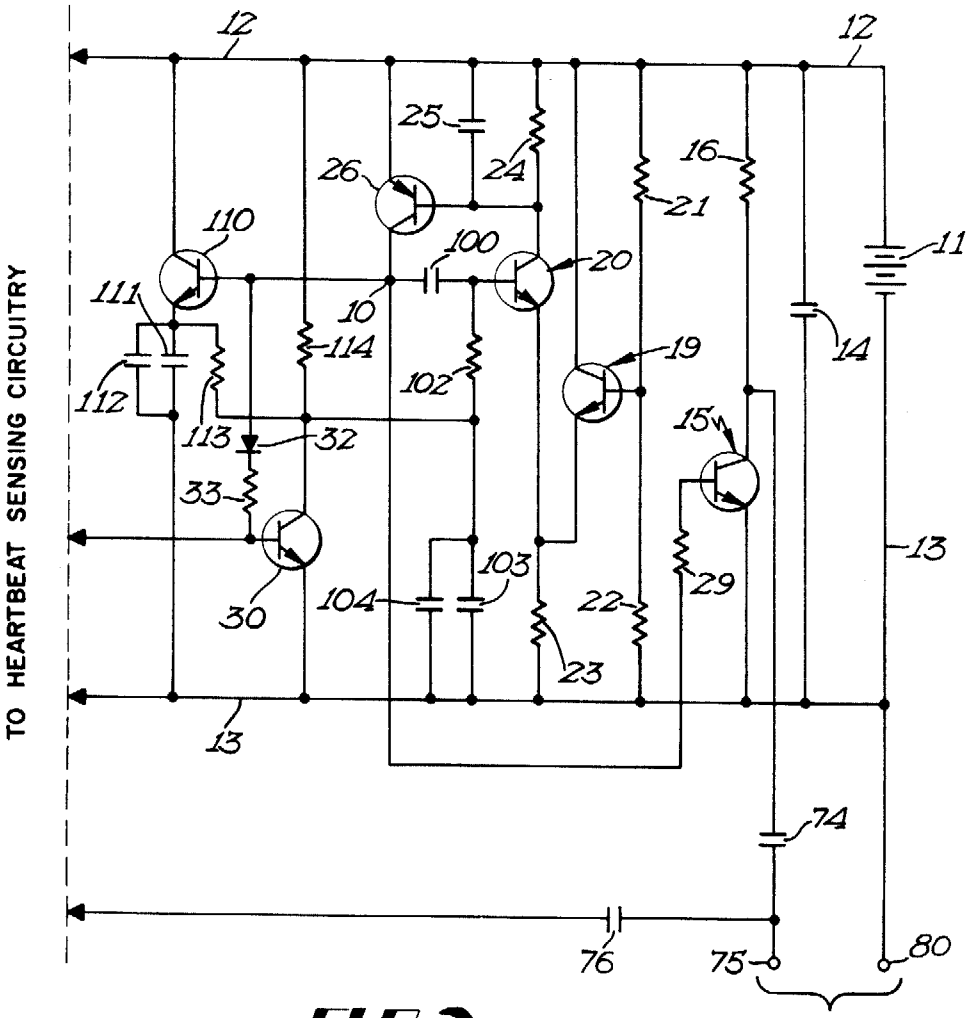
FIG. 2 is a variation of a portion of the schematic of FIG. 1 showing a second embodiment of this invention.

Referring now to FIG. 2 there is shown a portion of the schematic of FIG. 1 with necessary changes pertaining to a second embodiment of the invention. In FIG. 2, those circuit elements which are the same as in FIG. 1 bear the same number.

Therefore, in FIG. 2 there is again shown the pulse generator generally described as including transistors 19, 20, 26 and 30, along with their associated components. Transistor 15 again comprises the output transistor. However, in FIG. 2, junction 10 is connected to the base of transistor 20 through a capacitor 100, and to the base of a transistor 110. It is thus apparent that the on time of the pulse generator will be determined by the charge time of capacitor 100 of FIG. 2, as opposed to capacitor 28 of FIG. 1.

Transistor 110 has its collector connected directly to bus 12, while its emitter is connected to a capacitor 111 to bus 13. A bypass capacitor 112 is connected across capacitor 111. The collector of transistor 30 is connected through a resistor 114 to bus 12, and through a resistor 113 to the emitter of transistor 110. The collector of transistor 30 is also connected through a resistor 102 to the base of transistor 20, and through a capacitor 103 to bus 13. A bypass capacitor 104 is connected across capacitor 103. The base of transistor 30 is connected (not shown) to receive an input signal from the sensing amplifier whenever a natural heartbeat occurs, for example with circuitry similar to that shown in FIG. 1.

In operation, assume again that no natural heartbeats have been present and that the pulse generator of the pacer has been running at its normal repetition rate. Assume also that an output pulse has just commenced.

That means that the charge on capacitor 103 has built to a sufficiently positive level to turn on transistor 20. As described in the operation of the circuitry of FIG. 1 above, the turn-on of transistor 20 will cause the turn-on of transistor 26 causing a positive voltage rise at junction 10. This positive voltage rise will be felt at the base of transistor 15 to turn it on and cause capacitor 74 to discharge through the heart through terminals 75 and 80. The positive pulse at junction 10 will also be felt through capacitor 100 to keep transistor 20 and thus transistor 26 turned on. This voltage will be affective for the charge time of capacitor 100, which thus determines the output pulse width.

The positive pulse at junction 10 will also be felt through diode 32 and resistor 33 on the base of transistor 30 to turn it on and thus discharge capacitor 103 to prepare it for the next timing sequence. In addition, the positive pulse at junction 10 will be felt on the base of transistor 110 to turn it on causing capacitor 111 to charge.

Now assume that the output pulse has been completed and that transistor 20 turns off, thus turning off transistor 26 which removes the positive voltage at junction 10 to thus turn off transistors 15, 30 and 110. Capacitor 103 will have been generally completely discharged by the turn-on of transistor 30, and will commence its normal charge through the path comprising positive bus 12, resistor 114, through capacitor 103 to negative bus 13. However, because transistor 110 was on during the generated output pulse capacitor 111 will have received a charge. When the generated pulse is completed and transistor 110 turns off, the charge on capacitor 111 will discharge through the path comprising resistor 113, capacitor 103 and bus 13. Thus, in addition to its normal charge path, capacitor 103 received an additional charge from capacitor 111. This results in a faster charge time for capacitor 103 with a resulting increase in the frequency of the pulse generator. It is thus apparent that when there is a generated or stimulating output from the pulse generator, transistor 110 and capacitor 111 will operate to cause an increased generating frequency.

Assume now that there is a natural heartbeat felt at terminals 75 and 80. The natural heartbeat will be sensed at the sensing circuitry (not shown in FIG. 2) which can be the same as that shown in FIG. 1, for example. The resulting input from the sensing of the natural heartbeat will be felt on the base of transistor 30 thus discharging capacitor 103 with a resulting restart of the pulse generator off period. However, inasmuch as transistor 110 did not again turn on, there was no additional charge to capacitor 111, and therefore no extra charge available for capacitor 103. Thus, the charge time for capacitor 103 will be greater, causing a decreased pulse frequency following the natural heartbeat.

Should there be no further natural heartbeats before the next pulse generator output pulse, the generated pulse would again result in the turn-on of transistor 110 and an increase of the frequency of the pulse generator back to the stimulating rate.

It is thus apparent that the embodiment of FIG. 2 operates to provide the same function as the apparatus of FIG. 1. FIG. 1 provides a decrease in the pulse generator frequency in the presence of a natural heartbeat, while FIG. 2 provides an increase in the pulse generator frequency when there is no natural heartbeat, both embodiments thus providing a stimulating pulse at a first frequency, and a standby rate of a lower frequency as well as a minimum frequency.

The apparatus of both of the embodiments of the drawings are intended to be totally implantable within the body. The embodiments carry their own source of power, battery 11, and are adapted to be so constructed that all of the components are packaged in a substance of substances substantially inert to body fluids and tissue. Electrodes 75 and 80, shown schematically in the drawings, are adapted to be connected directly to the heart muscle in one of several manners well known in the art, and are made of an electrically conductive material which is also substantially inert to body fluids and tissue.

In FIG. 1 resister 36 is shown to be a variable resistor which may be used to vary the normal frequency of the pulse generator. In addition, capacitor 39 may be a variable capacitor or comprises a plurality of capacitors which are selectively connected in the circuit by a manual switch or the like, to thus provide means for selecting the standby or sentinel frequency of the pacer.

It is thus apparent that the novel apparatus of this invention provides a demand type pacer having circuitry for providing heart stimulating pulses at first rate and a lower pulse generating or standby rate in the presence of a natural heartbeat, and having further circuitry to cause asynchronous operation at a third rate in the presence of external electrical noise of a periodic nature.

What is claimed is:

1. In a demand type heart pacer including input and output means adapted to be connected to a heart, the input means connected to means for sensing natural heartbeats, the improvement comprising: pulse generator means connected to the output means and including timing circuit means operable to control output pulses from said generator means at a selected frequency; means connecting the means for sensing natural heartbeats to said pulse generator means for resetting said timing circuit means on the occurrence of a natural heartbeat; and further timing circuit means connected to said timing circuit means for changing the frequency of output pulses from said generator means for one pulse cycle following a pulse cycle in which a natural heartbeat occurs.

2. In a demand heart pacemaker including power supply means, sensing means for detecting a natural heartbeat, pulse generator means for supplying pulses to stimulate a heartbeat and means for connecting the sensing means and generator means to a heart, the improvement comprising: resistor means and first capacitor means serially connected across the power supply means; said first capacitor means connected to the pulse generator means for controlling the frequency of pulses therefrom according to the charging time of said first capacitor means; and circuit means including second capacitor means connected to said first capacitor means for selectively changing the charge time of said first capacitor means for one pulse cycle following a pulse cycle in which the natural heartbeat occurs.

3. In a demand type heart pacer including input and output means adapted to be connected to a heart, the input means connected to means for sensing natural heartbeats, the improvement comprising: pulse generator means connected to the output means and including timing circuit means operable to control output pulses from said generator means at a selected frequency; and further means connecting the means for sensing natural heartbeats to said pulse generator means for resetting said timing circuit means on the occurrence of a natural heartbeat and including further timing circuit means operably connected to said timing circuit means on the occurrence of a natural heartbeat for decreasing the frequency of output pulses from said generator means for one pulse cycle following a pulse cycle in which an natural heartbeat occurs.

4. The apparatus of claim 3 in which: said timing circuit means includes resistor means and capacitor means connected in an RC timing circuit; and said further timing circuit means includes further capacitor means and switch means for connecting said further capacitor means into said RC timing circuit.

5. The apparatus of claim 3 in which: said timing circuit means includes serially connected resistance means and capacitance means; and said further timing circuit means includes further capacitance means, means including diode means connecting said further capacitance means across said capacitance means, said diode means poled to prevent said further capacitance means from discharging into said capacitance means, and switch means connected across said further capacitance means and connected to said further means for discharging all said capacitance means on the occurrence of a natural heartbeat.

6. In a demand heart pacer including power supply means, sensing means for detecting a natural heartbeat, pulse generator means for supplying pulses to stimulate a heartbeat and means for connecting the sensing means and generator means to a heart, the improvement comprising: resistor means and first capacitor means serially connected across the power supply means; said first capacitor means connected to the pulse generator means for controlling the frequency of pulses therefrom according to the charging time of said first capacitor means; and circuit means connected to the sensing means and to said first capacitor means and operable in response to the occurrence of a natural heartbeat for changing the charge time of said first capacitor means for one pulse cycle following a pulse cycle in which the natural heartbeat occurs.

7. The apparatus of claim 6 in which said circuit means comprises, second capacitor means; switch means connected between the sensing means and said first and second capicitor means for connecting said first and second capacitor means in parallel charging paths in response to the occurrence of a natural heartbeat for increasing the charging time of said first capacitor means.

8. The apparatus of claim 6 including noise responsive means for blocking repetitive noise signals for said circuit means comprising: capacitor means having an input plate connected to the sensing means and an output plate connected to said circuit means; a first discharge path for said capacitor means connected to said output plate and including serially connected diode means and resistor means, said diode means poled to pass current of a first polarity, said resistor means having a resistance value selected for generally fast discharge of said capacitor means; and a second discharge path for said capacitor means connected to said output plate and including further resistor means having a resistance value selected for generally slow discharge of said capacitor means for charging said capacitor means with repeated noise pulses of a second polarity at a frequency above that of the normal heartbeat range to block further of said noise pulses of the second polarity.

9. In a demand pacer having input and output means adapted to be connected to a heart, pulse generator means connected to the output means and sensing means for detecting natural heartbeats connected to the input means, the improvement comprising: resistor means and first capacitor means connected in an RC timing circuit and to the pulse generator means for controlling the frequency of the pulse generator means according to the charge time of said first capacitor means; first switch means connected to said first capacitor means and to the pulse generator means, and actuated by an output pulse from the pulse generator means to discharge said first capacitor means; second capacitor means; means including diode means connecting said second capacitor to said first capacitor means, said diode means poled to permit said first and second capacitor means to charge in parallel and to prevent the discharge of said second capacitor means by said first switch means; and second switch means connected to said second capacitor means and the sensing means, and actuated by a natural heartbeat to discharge said first and second capacitor means.

10. The apparatus of claim 9 including noise responsive means comprising: third capacitor means connected between the sensing means and said second switch means; second resistor means; further diode means; third resistor means; means for connecting said second resistor means across said third capacitor means to provide a first discharge path, and for connecting said further diode means and said third resistor means across said third capacitor means to provide a second discharge path for one electrical polarity; and said second and third resistor means having resistances selected to make the time constant of said first discharge path substantially greater than the time constant of said second discharge path.

11. In a demand type heart pacer including input and output means adapted to be connected to a heart, the input means connected to means for sensing natural heartbeats, the improvement comprising: pulse generator means connected to the output means and including timing circuit means operable to control output pulses from said generator means at a selected frequency; further means connecting the means for sensing natural heartbeats to said pulse generator means for resetting said timing circuit means on the occurrence of a natural heartbeat; and further timing circuit means operably connected to said timing circuit means on the occurrence of an output pulse from said pulse generator for increasing the frequency of output pulses from said generator means for one pulse cycle following the absence of a natural heartbeat.

12. The apparatus of claim 11 in which: said timing circuit means includes resistor means and capacitor means connected in an RC timing circuit; and said further timing circuit means includes further capacitor means connected to said RC timing circuit and switch means operable on the occurrence of an output pulse from said pulse generator for charging said further capacitor means.

13. The apparatus of claim 11 in which: said timing circuit means includes serially connected resistance means and capacitance means; and said further timing circuit means includes further capacitance means, means connecting said further capacitance means across said capacitance means, switch means adapted to connect said further capacitance means across a source of energy, and means connecting said switch means to said pulse generator for receiving pulses therefrom.

14. In a [demand] heart pacer including power supply means, pulse generator means for supplying stimulating pulses to a heart and means for connecting the generator means to a heart, the improvement comprising: resistor means and first capacitor means serially connected across the power supply means; said first capacitor means connected to the pulse generator means for controlling the frequency of pulses therefrom according to the charging time of said first capacitor means; and circuit means connected to the pulse generator and to said first capacitor means and operable in response to the occurrence of a generated stimulating pulse for changing the charge time of said first capacitor means.

15. The apparatus of claim 14 in which said circuit means comprises: second capacitor means; switch means connecting said second capacitor means across the power supply; said switch means connected to and controllable by the pulse generator for charging said second capacitor means on the occurrence of a generated stimulating pulse; and means connecting said first and second capacitor means in parallel for decreasing the charging time of said first capacitor means.

16. The apparatus of claim 14 including *sensing means for detecting a natural heartbeat and* noise responsive means for blocking repetitive noise signals from said circuit means comprising: capacitor means having an input plate connected to the sensing means and an output plate connected to said circuit means; a first discharge path for said capacitor means connected to said output plate and including serially connected diode means and resistor means, said diode means poled to pass current of a first polarity, said resistor means having a resistance value selected for generally fast discharge of said capacitor means; and a second discharge path for said capacitor means connected to said output plate and including further resistor means having a resistance value selected for generally slow discharge of said capacitor means for charging said capacitor means with repeated noise pulses of a second polarity at a frequency above that of the normal heartbeat range to block further of said noise pulses of the second polarity.

17. In a demand pacer having input and output means adapted to be connected to a heart pulse generator means connected to the output means and sensing means for detecting natural heartbeats connected to the input means, the improvement comprising: resistor means and first capacitor means connected in an RC timing circuit and to the pulse generator means for controlling the frequency of the pulse generator means according to the charge time of said first capacitor means; first switch means connected to said first capacitor means and to the sensing means; and actuated by a pulse from the sensing means to discharge said first capacitor means; second capacitor means; means connecting said second capacitor to said first capacitor means for discharging said second capacitor into said first capacitor; and second switch means connected to said second capacitor means and the pulse generator means and actuated by a generated pulse to charge said second capacitor means.

18. The apparatus of claim 17 including noise readapted to be connected to a heart, the input means connected between the sensing means and said first switch means; second resistor means; diode means; third resistor means; means for connecting said second resistor means across said third capacitor means to provide a first discharge path, and for connecting said diode means and said third resistor means across said third capacitor means to provide a second discharge path for one electrical polarity; and said second and third resistor means having resistances selected to make the time constant of said first discharge path substantially greater than the time constant of said second discharge path.

19. In a heart pacer including input and output means adapted to be connected to a heater, the input means connected to sensing means for detecting a natural heartbeat and the output means connected to pulse generator means for supplying pulses to stimulate a heart, noise responsive means for preventing repetitive noise signals sensed by the sensing means from disabling the pulse generator means comprising: capacitor means having an input plate connected to the sensing means and an output plate connected to the pulse generator means; a first discharge path for said capacitor means connected to said output plate and including serially connected diode means and resistor means, said diode means poled to pass current of a first polarity, said resistor means having a resistance value selected for generally fast discharge of said capacitor means; and a second discharge path for said capacitor means connected to said output plate and including further resistor means having a resistance value selected for generally slow discharge of said capacitor means for charging said capacitor means with repeated noise pulses of a second polarity at a frequency above that of the normal heartbeat range to block further of said noise pulses of the second polarity.

20. In a demand type heart pacer having pulse generator means including timing means operable to control ouput pulses from the generator means at a selected frequency, having sensing means for sensing natural heartbeats including means refractory to applied signals for a predetermined refractory period following each pacer pulse, having reset means, operatively connected to the pulse generator means, for resetting the timing means upon occurrence of each output pulse and having means connected to the pulse generator means and the sensing means and adapted to be connected to a heart; the improvement comprising: further means, operatively connecting the sensing means to the pulse generator means, for resetting the timing means for a predetermined limited time upon termination of the refractory period in response to repetitive signals, sensed by the sensing means, which exceed a predetermined rate greater than a natural heart rate and including means *automatically* for preventing the timing means from continuous resetting in response to such repetitive signals, thereby decreasing the frequency of output pulses from the pulse generator means and causing the pacer to operate asynchronously.

References Cited

The following references, cited by the Examiner, are of record in the patented file of this patent or the original patent.

UNITED STATES PATENTS

| | | | |
|---|---|---|---|
| 3,431,912 | 3/1969 | Kelley | 128—419 P |
| 3,345,990 | 10/1967 | Berkovits | 128—419 P |
| 3,528,428 | 9/1970 | Berkovits | 128—419 P |
| 3,050,695 | 8/1962 | DuVall | 128—419 P |
| 3,181,535 | 5/1965 | Milinowski | 128—422 |
| 3,345,990 | 10/1967 | Berkovits | 128—419 P |

FOREIGN PATENTS 826,766 1/1960 Great Britain.

WILLIAM E. KAMM, Primary Examiner

U.S. Cl. X.R.

128—422